United States Patent
Gocal et al.

(10) Patent No.: US 10,612,035 B2
(45) Date of Patent: Apr. 7, 2020

(54) EPSPS MUTANTS

(71) Applicant: CIBUS US LLC, San Diego, CA (US)

(72) Inventors: Greg F. W. Gocal, San Diego, CA (US); Mark E. Knuth, Poway, CA (US); Peter R. Beetham, Carlsbad, CA (US)

(73) Assignee: CIBUS US LLC, San Diego, CA (US)

( * ) Notice: Subject to any disclaimer, the term of this patent is extended or adjusted under 35 U.S.C. 154(b) by 0 days.

(21) Appl. No.: 16/040,278

(22) Filed: Jul. 19, 2018

(65) Prior Publication Data

US 2018/0327774 A1  Nov. 15, 2018

Related U.S. Application Data

(60) Continuation of application No. 13/621,662, filed on Sep. 17, 2012, now abandoned, which is a division of application No. 12/160,725, filed as application No. PCT/US2007/000591 on Jan. 10, 2007, now Pat. No. 8,268,622.

(60) Provisional application No. 60/758,439, filed on Jan. 12, 2006.

(51) Int. Cl.
*C12N 15/82*  (2006.01)
*C12N 9/10*  (2006.01)

(52) U.S. Cl.
CPC ....... *C12N 15/8275* (2013.01); *C12N 9/1092* (2013.01); *C12N 15/8213* (2013.01)

(58) Field of Classification Search
CPC ................................................. C12N 15/8275
See application file for complete search history.

(56) References Cited

U.S. PATENT DOCUMENTS 8,268,622 B2 * 9/2012 Gocal .................. C12N 9/1092
435/468

FOREIGN PATENT DOCUMENTS

GB  2 326 163 A  * 12/1998  ......... C12N 15/8275

OTHER PUBLICATIONS

Baerson et al, Plant Physiology 129: 1265-1275 (Year: 2002).*
Genbank Accession AF360224, United States National Library of Science, Bethesda, Maryland (Year: 2002).*
Genbank Accession AAK25934, United States National Library of Science, Bethesda, Maryland (Year: 2002).*

* cited by examiner

*Primary Examiner* — David H Kruse
(74) *Attorney, Agent, or Firm* — Acuity Law Group, PC; Michael A. Whittaker

(57) ABSTRACT

The present invention relates to the production of a non-transgenic plant resistant or tolerant to a herbicide of the phosphonomethylglycine family, e.g., glyphosate. The present invention also relates to the use of a recombinagenic oligonucleobase to make a desired mutation in the chromosomal or episomal sequences of a plant in the gene encoding for 5-enol pyruvylshikimate-3-phosphate synthase (EPSPS). The mutated protein, which substantially maintains the catalytic activity of the wild-type protein, allows for increased resistance or tolerance of the plant to a herbicide of the phosphonomethylglycine family, and allows for the substantially normal growth or development of the plant, its organs, tissues or cells as compared to the wild-type plant irrespective of the presence or absence of the herbicide. Additionally the present invention relates to mutant *E. coli* cells that contain mutated EPSPS genes.

2 Claims, 5 Drawing Sheets

Specification includes a Sequence Listing.

Polymorphisms mapped on the E. coli AroA

```
  1 MESLTLQPIA RVDGTINLPG SKSVSNRALL LAALAHGKTV LTNLLDSDDV
 51 RHMLNALTAL GVSYTLSADR TRCEIIGNGG PLHAEGALEL FLGNAGTAMR
101 PLAAALCLGS NDIVLTGEPR MKERPIGHLV DALRLGGAKI TYLEQENYPP
151 LRLQGGFTGG NVDVDGSVSS QFLTALLMTA PLAPEDTVIR IKGDLVSKPY
201 IDITLNLMKT FGVEIENQHY QQFVVKGGQS YQSPGTYLVE GDASSASYFL
251 AAAAIKGGTV KVTGIGRNSM QGDIRFADVL EKMGATICWG DDYISCTRGE
301 LNAIDMDMNH IPDAAMTIAT AALFAKGTTT LRNIYNWRVK ETDRLFAMAT
351 ELRKVGAEVE EGHDYIRITP PEKVNFAEIA TYNDHRMAMC FSLVALSDTP
401 VTILDPKCTA KTFPDYFEQL ARISQAA
```

Box I L82S
Box II V374L

FIG. 1

AtEPSPS cDNA - At2g45300
translated from Genbank accession NM_130093

```
  1 MAQVSRICNG VQNPSLISNL SKSSQRKSPL SVSLKTQQHP RAYPISSSWG
 51 LKKSGMTLIG SELRPLKVMS SVSTAEKASE IVLQPIREIS GLIKLPGSKS
101 LSNRILLLAA LSEGTTVVDN LLNSDDINYM LDALKRLGLN VETDSENNRA
151 VVEGCGGIFP ASIDSKSDIE LYLGNAGTAM RPLTAAVTAA GGNASYVLDG
201 VPRMRERPIG DLVVGLKQLG ADVECTLGTN CPPVRVNANG GLPGGKVKLS
251 GSISSQYLTA LLMSAPLALG DVEIEIVDKL ISVPYVEMTL KLMERFGVSV
301 EHSDSWDRFF VKGGQKYKSP GNAYVEGDAS SASYFLAGAA ITGETVTVEG
351 CGTTSLQGDV KFAEVLEKMG CKVSWTENSV TVTGPPRDAF GMRHLRAIDV
401 NMNKMPDVAM TLAVVALFAD GPTTIRDVAS WRVKETERMI AICTELRKLG
451 ATVEEGSDYC VITPPKKVKT AEIDTYDDHR MAMAFSLAAC ADVPITINDP
501 GCTRKTFPDY FQVLERITKH
```

FIG. 2

AtEPSPS cDNA - At1g48860
translated from Genbank accession AF360224T

```
  1 MASSLTSKSI LGCTKPASSS FLPSELRRLS SPAVQISLHS QTRKNFRQSW
 51 GLKKSDLMLN GSEIRPVKVR ASVSTAEKAS EIVLQPIREI SGLIKLPGSK
101 SLSNRILLLA ALSEGTTVVD NLLNSDDINY MLDALKILGL NVETHSENNR
151 AVVEGCGGVF PASIDSKSDI ELYLGNAGTA MRPLTAAVTA AGGNASYVLD
201 GVPRMRERPI GDLVVGLKQL GADVECTLGT NCPPVRVNAN GGLPGGKVKL
251 SGSISSQYLT ALLMAAPLAL GDVEIEIVDK LISVPYVEMT LKLMERFGVS
301 AEHSESWDRF FVKGGQKYKS PGNAYVEGDA SSASYFLAGA AITGETVTVE
351 GCGTTSLQGD VKFAEVLEKM GCKVSWTENS VTVTGPSRDA FGMRHLRAID
401 VNMNKMPDVA MTLAVVALFA DGPTTIRDVA SWRVKETERM IAICTELRKL
451 GATVEEGSDY CVITPPKKVK PAEIDTYDDH RMAMAFSLAA CADVPITIND
501 PGCTRKTFPD YFQVLERITK H
```

FIG. 3

BnEPSPS cDNA - BN-2 2-23

```
  1 MAQASRICQN PCVISNLSKS NQRKSPFSVS LKTHQQQRGA YQISSWGLKK
 51 SNNGSVIRPV KVMASVSTAE KASEIVLQPI REISGLIKLP GSKSLSNRIL
101 LLAALSEGTT VVDNLLNSDD INYMLDALNK LGLNVERDSE NNRAVVEGCG
151 GIFPASLDSK GDIELYLGNA GTAMRPLTAA VTAAGGNASY VLDGVPRMRE
201 RPIGDLVVGL KQLGADVECT LGTNCPPVRV NANGGLPGGK VKLSGSISSQ
251 YLTALLMAAP LALGDVEIEI IDKLISVPYV EMTLKLMERF GVSAEHSDSW
301 DRFFVKGGQK YKSPGNAYVE GDASSASYFL AGAAITGETV TVEGCGTTSL
351 QGDVKFAEVL EKMGCKVSWT ENSVTVTGPS RDAFGMRHLR AVDVNMNKMP
401 DVAMTLAVVA LFADGPTTIR DVASWRVKET ERMIAICTEL RKLGATVEEG
451 SDYCVITPPA KLKPAEIDTY DDHRMAMAFS LAACADVPVT IKDPGCTRKT
501 FPDYFQVLES ITKH
```

FIG. 4

BnEPSPS cDNA - 2-28 from X51475 gDNA translation

```
  1 MAQSSRICHG VQNPCVIISN LSKSNQNKSP FSVSLKTHQP RASSWGLKKS
 51 GTMLNGSVIR PVKVTASVST SEKASEIVLQ PIREISGLIK LPGSKSLSNR
101 ILLLAALSEG TTVVDNLLNS DDINYMLDAL KKLGLNVERD SVNNRAVVEG
151 CGGIFPASLD SKSDIELYLG NAGTAMRPLT AAVTAAGGNA SYVLDGVPRM
201 RERPIGDLVV GLKQLGADVE CTLGTNCPPV RVNANGGLPG GKVKLSGSIS
251 SQYLTALLMA APLALGDVEI EIIDKLISVP YVEMTLKLME RFGVSAEHSD
301 SWDRFFVKGG QKYKSPGNAY VEGDASSASY FLAGAAITGE TVTVEGCGTT
351 SLQGDVKFAE VLEKMGCKVS WTENSVTVTG PSRDAFGMRH LRAVDVNMNK
401 MPDVAMTLAV VALFADGPTT IRDVASWRVK ETERMIAICT ELRKLGATVE
451 EGSDYCVITP PAKVKPAEID TYDDHRMAMA FSLAACADVP VTIKDPGCTR
501 KTFPDYFQVL ESITKH
```

FIG. 5

SEQUENCE LISTING

<160> NUMBER OF SEQ ID NOS: 21

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence: Synthetic
      recombinagenic oligonucleobase designed to cause
      a point mutation in Brussica napus

<400> SEQUENCE: 1
atgcaggaac agccatgcgt tcacttacgg ctgcagttac t                 41

<210> SEQ ID NO 2
<211> LENGTH: 46
<212> TYPE: DNA
<213> ORGANISM: Artificial Sequence
<220> FEATURE:
<223> OTHER INFORMATION: Description of Artificial Sequence: Synthetic
      recombinagenic oligonucleobase designed to cause
      a point mutation in oryza sativa

<400> SEQUENCE: 2
ggaacgctgg aactgcaatg cgagcattga cagcagccgt gactgc            46

-continued

```
<210> SEQ ID NO 3
<211> LENGTH: 42
<212> TYPE: DNA
<213> ORGANISM: Arabidopsis sp.
<220> FEATURE:
<223> OTHER INFORMATION: native EPSPS gene

<400> SEQUENCE: 3
ctttacctcg gtaatgcagg aacagcaatg cgtccactta cc            42

<210> SEQ ID NO 4
<211> LENGTH: 42
<212> TYPE: DNA
<213> ORGANISM: Arabidopsis sp.
<220> FEATURE:
<223> OTHER INFORMATION: mutated EPSPS gene

<400> SEQUENCE: 4
ctttacctcg gtaatgcagg agcagcaatg cgtccactta cc            42

<210> SEQ ID NO 5
<211> LENGTH: 35
<212> TYPE: DNA
<213> ORGANISM: Arabidopsis sp.
<220> FEATURE:
<223> OTHER INFORMATION: native EPSPS gene

<400> SEQUENCE: 5
ggatgtggcg ggatattccc agcttccata gattc            35

<210> SEQ ID NO 6
<211> LENGTH: 35
<212> TYPE: DNA
<213> ORGANISM: Arabidopsis sp.
<220> FEATURE:
<223> OTHER INFORMATION: mutated EPSPS gene

<400> SEQUENCE: 6
ggatgtggcg ggatatcccc agcttccata gattc            35

<210> SEQ ID NO 7
<211> LENGTH: 36
<212> TYPE: DNA
<213> ORGANISM: Arabidopsis sp.
<220> FEATURE:
<223> OTHER INFORMATION: native EPSPS gene

<400> SEQUENCE: 7
gcaggaacag caatgcgtcc acttaccgct gcggtc            36

<210> SEQ ID NO 8
<211> LENGTH: 36
<212> TYPE: DNA
<213> ORGANISM: Arabidopsis sp.
<220> FEATURE:
<223> OTHER INFORMATION: mutated EPSPS gene

<400> SEQUENCE: 8
gcaggaacag caatgcgttg ccttaccgct gcggtc            36

<210> SEQ ID NO 9
<211> LENGTH: 36
<212> TYPE: DNA
<213> ORGANISM: Arabidopsis sp.
<220> FEATURE:
<223> OTHER INFORMATION: native EPSPS gene
```

<400> SEQUENCE: 9
cctcggtaat gcaggaacag caatgcgtcc acttac        36

<210> SEQ ID NO 10
<211> LENGTH: 36
<212> TYPE: DNA
<213> ORGANISM: Arabidopsis sp.
<220> FEATURE:
<223> OTHER INFORMATION: mutated EPSPS gene

<400> SEQUENCE: 10
cctcggtaat gcaggaatag caatgcgtgc acttac        36

<210> SEQ ID NO 11
<211> LENGTH: 38
<212> TYPE: DNA
<213> ORGANISM: Arabidopsis sp.
<220> FEATURE:
<223> OTHER INFORMATION: native EPSPS gene

<400> SEQUENCE: 11
ggtcactgct gcaggtggaa acgcaagtta tgtgcttg        38

<210> SEQ ID NO 12
<211> LENGTH: 38
<212> TYPE: DNA
<213> ORGANISM: Arabidopsis sp.
<220> FEATURE:
<223> OTHER INFORMATION: mutated EPSPS gene

<400> SEQUENCE: 12
ggtcactgct gcaggtggag ccgcaagtta tgtgcttg        38

<210> SEQ ID NO 13
<211> LENGTH: 36
<212> TYPE: DNA
<213> ORGANISM: Arabidopsis sp.
<220> FEATURE:
<223> OTHER INFORMATION: native EPSPS gene

<400> SEQUENCE: 13
cctcggtaat gcaggaacag caatgcgtcc acttac        36

<210> SEQ ID NO 14
<211> LENGTH: 36
<212> TYPE: DNA
<213> ORGANISM: Arabidopsis sp.
<220> FEATURE:
<223> OTHER INFORMATION: mutated EPSPS gene

<400> SEQUENCE: 14
cctcggtaat gcaggagcag caatgcgtgc acttac        36

<210> SEQ ID NO 15
<211> LENGTH: 36
<212> TYPE: DNA
<213> ORGANISM: Arabidopsis sp.
<220> FEATURE:
<223> OTHER INFORMATION: native EPSPS gene

<400> SEQUENCE: 15
cctcggtaat gcaggaacag caatgcgtcc acttac        36

<210> SEQ ID NO 16
<211> LENGTH: 36

```
<212> TYPE: DNA
<213> ORGANISM: Arabidopsis sp.
<220> FEATURE:
<223> OTHER INFORMATION: mutated EPSPS gene

<400> SEQUENCE: 16
cctcggtaat gcaggagcag caatgcgtac acttac                                    36

<210> SEQ ID NO 17
<211> LENGTH: 427
<212> TYPE: PRT
<213> ORGANISM: Escherichia coli

<400> SEQUENCE: 17
```

| Met | Glu | Ser | Leu | Thr | Leu | Gln | Pro | Ile | Ala | Arg | Val | Asp | Gly | Thr | Ile |
|---|---|---|---|---|---|---|---|---|---|---|---|---|---|---|---|
| 1 | | | | 5 | | | | | 10 | | | | | 15 | |

| Asn | Leu | Pro | Gly | Ser | Lys | Ser | Val | Ser | Asn | Arg | Ala | Leu | Leu | Leu | Ala |
|---|---|---|---|---|---|---|---|---|---|---|---|---|---|---|---|
| | | | 20 | | | | | 25 | | | | | 30 | | |

| Ala | Leu | Ala | His | Gly | Lys | Thr | Val | Leu | Thr | Asn | Leu | Leu | Asp | Ser | Asp |
| | | 35 | | | | | 40 | | | | | 45 | | | |

| Asp | Val | Arg | His | Met | Leu | Asn | Ala | Leu | Thr | Ala | Leu | Gly | Val | Ser | Tyr |
| | 50 | | | | | 55 | | | | | 60 | | | | |

| Thr | Leu | Ser | Ala | Asp | Arg | Thr | Arg | Cys | Glu | Ile | Ile | Gly | Asn | Gly | Gly |
| 65 | | | | | 70 | | | | | 75 | | | | | 80 |

| Pro | Leu | His | Ala | Glu | Gly | Ala | Leu | Glu | Leu | Phe | Leu | Gly | Asn | Ala | Gly |
| | | | | 85 | | | | | 90 | | | | | 95 | |

| Thr | Ala | Met | Arg | Pro | Leu | Ala | Ala | Ala | Leu | Cys | Leu | Gly | Ser | Asn | Asp |
| | | | 100 | | | | | 105 | | | | | 110 | | |

| Ile | Val | Leu | Thr | Gly | Glu | Pro | Arg | Met | Lys | Glu | Arg | Pro | Ile | Gly | His |
| | | 115 | | | | | 120 | | | | | 125 | | | |

| Leu | Val | Asp | Ala | Leu | Arg | Leu | Gly | Gly | Ala | Lys | Ile | Thr | Tyr | Leu | Glu |
| | 130 | | | | | 135 | | | | | 140 | | | | |

| Gln | Glu | Asn | Tyr | Pro | Pro | Leu | Arg | Leu | Gln | Gly | Gly | Phe | Thr | Gly | Gly |
| 145 | | | | | 150 | | | | | 155 | | | | | 160 |

| Asn | Val | Asp | Val | Asp | Gly | Ser | Val | Ser | Ser | Gln | Phe | Leu | Thr | Ala | Leu |
| | | | | 165 | | | | | 170 | | | | | 175 | |

| Leu | Met | Thr | Ala | Pro | Leu | Ala | Pro | Glu | Asp | Thr | Val | Ile | Arg | Ile | Lys |
| | | | 180 | | | | | 185 | | | | | 190 | | |

| Gly | Asp | Leu | Val | Ser | Lys | Pro | Tyr | Ile | Asp | Ile | Thr | Leu | Asn | Leu | Met |
| | | 195 | | | | | 200 | | | | | 205 | | | |

| Lys | Thr | Phe | Gly | Val | Glu | Ile | Glu | Asn | Gln | His | Tyr | Gln | Gln | Phe | Val |
| | 210 | | | | | 215 | | | | | 220 | | | | |

| Val | Lys | Gly | Gly | Gln | Ser | Tyr | Gln | Ser | Pro | Gly | Thr | Tyr | Leu | Val | Glu |
| 225 | | | | | 230 | | | | | 235 | | | | | 240 |

| Gly | Asp | Ala | Ser | Ser | Ala | Ser | Tyr | Phe | Leu | Ala | Ala | Ala | Ile | Lys |
| | | | | 245 | | | | | 250 | | | | | 255 |

| Gly | Gly | Thr | Val | Lys | Val | Thr | Gly | Ile | Gly | Arg | Asn | Ser | Met | Gln | Gly |
| | | | 260 | | | | | 265 | | | | | 270 | | |

| Asp | Ile | Arg | Phe | Ala | Asp | Val | Leu | Glu | Lys | Met | Gly | Ala | Thr | Ile | Cys |
| | | 275 | | | | | 280 | | | | | 285 | | | |

| Trp | Gly | Asp | Asp | Tyr | Ile | Ser | Cys | Thr | Arg | Gly | Glu | Leu | Asn | Ala | Ile |
| | 290 | | | | | 295 | | | | | 300 | | | | |

| Asp | Met | Asp | Met | Asn | His | Ile | Pro | Asp | Ala | Ala | Met | Thr | Ile | Ala | Thr |
| 305 | | | | | 310 | | | | | 315 | | | | | 320 |

| Ala | Ala | Leu | Phe | Ala | Lys | Gly | Thr | Thr | Thr | Leu | Arg | Asn | Ile | Tyr | Asn |
| | | | | 325 | | | | | 330 | | | | | 335 | |

```
Trp Arg Val Lys Glu Thr Asp Arg Leu Phe Ala Met Ala Thr Glu Leu
            340                 345                 350

Arg Lys Val Gly Ala Glu Val Glu Gly His Asp Tyr Ile Arg Ile
        355                 360                 365

Thr Pro Pro Glu Lys Val Asn Phe Ala Glu Ile Ala Thr Tyr Asn Asp
    370                 375                 380

His Arg Met Ala Met Cys Phe Ser Leu Val Ala Leu Ser Asp Thr Pro
385                 390                 395                 400

Val Thr Ile Leu Asp Pro Lys Cys Thr Ala Lys Thr Phe Pro Asp Tyr
                405                 410                 415

Phe Glu Gln Leu Ala Arg Ile Ser Gln Ala Ala
                420                 425

<210> SEQ ID NO 18
<211> LENGTH: 520
<212> TYPE: PRT
<213> ORGANISM: Arabidopsis thaliana

<400> SEQUENCE: 18

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Glu Lys Ala Ser Glu
65                  70                  75                  80

Ile Val Leu Gln Pro Ile Arg Glu Ile Ser Gly Leu Ile Lys Leu Pro
                85                  90                  95

Gly Ser Lys Ser Leu Ser Asn Arg Ile Leu Leu Leu Ala Ala Leu Ser
            100                 105                 110

Glu Gly Thr Thr Val Val Asp Asn Leu Leu Asn Ser Asp Asp Ile Asn
        115                 120                 125

Tyr Met Leu Asp Ala Leu Lys Arg Leu Gly Leu Asn Val Glu Thr Asp
    130                 135                 140

Ser Glu Asn Asn Arg Ala Val Val Glu Gly Cys Gly Gly Ile Phe Pro
145                 150                 155                 160

Ala Ser Ile Asp Ser Lys Ser Asp Ile Glu Leu Tyr Leu Gly Asn Ala
                165                 170                 175

Gly Thr Ala Met Arg Pro Leu Thr Ala Ala Val Thr Ala Ala Gly Gly
            180                 185                 190

Asn Ala Ser Tyr Val Leu Asp Gly Val Pro Arg Met Arg Glu Arg Pro
        195                 200                 205

Ile Gly Asp Leu Val Val Gly Leu Lys Gln Leu Gly Ala Asp Val Glu
    210                 215                 220

Cys Thr Leu Gly Thr Asn Cys Pro Pro Val Arg Val Asn Ala Asn Gly
225                 230                 235                 240

Gly Leu Pro Gly Gly Lys Val Lys Leu Ser Gly Ser Ile Ser Ser Gln
                245                 250                 255

Tyr Leu Thr Ala Leu Leu Met Ser Ala Pro Leu Ala Leu Gly Asp Val
            260                 265                 270

Glu Ile Glu Ile Val Asp Lys Leu Ile Ser Val Pro Tyr Val Glu Met
```

```
                    275                 280                 285
Thr Leu Lys Leu Met Glu Arg Phe Gly Val Ser Val Glu His Ser Asp
    290                 295                 300

Ser Trp Asp Arg Phe Phe Val Lys Gly Gly Gln Lys Tyr Lys Ser Pro
305                 310                 315                 320

Gly Asn Ala Tyr Val Glu Gly Asp Ala Ser Ala Ser Tyr Phe Leu
                325                 330                 335

Ala Gly Ala Ala Ile Thr Gly Glu Thr Val Thr Val Gly Cys Gly
                340                 345                 350

Thr Thr Ser Leu Gln Gly Asp Val Lys Phe Ala Glu Val Leu Glu Lys
            355                 360                 365

Met Gly Cys Lys Val Ser Trp Thr Glu Asn Ser Val Thr Val Thr Gly
    370                 375                 380

Pro Pro Arg Asp Ala Phe Gly Met Arg His Leu Arg Ala Ile Asp Val
385                 390                 395                 400

Asn Met Asn Lys Met Pro Asp Val Ala Met Thr Leu Ala Val Val Ala
                405                 410                 415

Leu Phe Ala Asp Gly Pro Thr Thr Ile Arg Asp Val Ala Ser Trp Arg
            420                 425                 430

Val Lys Glu Thr Glu Arg Met Ile Ala Ile Cys Thr Glu Leu Arg Lys
    435                 440                 445

Leu Gly Ala Thr Val Glu Glu Gly Ser Asp Tyr Cys Val Ile Thr Pro
    450                 455                 460

Pro Lys Lys Val Lys Thr Ala Glu Ile Asp Thr Tyr Asp Asp His Arg
465                 470                 475                 480

Met Ala Met Ala Phe Ser Leu Ala Ala Cys Ala Asp Val Pro Ile Thr
                485                 490                 495

Ile Asn Asp Pro Gly Cys Thr Arg Lys Thr Phe Pro Asp Tyr Phe Gln
            500                 505                 510

Val Leu Glu Arg Ile Thr Lys His
    515                 520

<210> SEQ ID NO 19
<211> LENGTH: 521
<212> TYPE: PRT
<213> ORGANISM: Arabidopsis thaliana

<400> SEQUENCE: 19

Met Ala Ser Ser Leu Thr Ser Lys Ser Ile Leu Gly Cys Thr Lys Pro
1               5                   10                  15

Ala Ser Ser Ser Phe Leu Pro Ser Glu Leu Arg Arg Leu Ser Ser Pro
                20                  25                  30

Ala Val Gln Ile Ser Leu His Ser Gln Thr Arg Lys Asn Phe Arg Gln
            35                  40                  45

Ser Trp Gly Leu Lys Lys Ser Asp Leu Met Leu Asn Gly Ser Glu Ile
    50                  55                  60

Arg Pro Val Lys Val Arg Ala Ser Val Ser Thr Ala Glu Lys Ala Ser
65                  70                  75                  80

Glu Ile Val Leu Gln Pro Ile Arg Glu Ile Ser Gly Leu Ile Lys Leu
                85                  90                  95

Pro Gly Ser Lys Ser Leu Ser Asn Arg Ile Leu Leu Leu Ala Ala Leu
            100                 105                 110

Ser Glu Gly Thr Thr Val Val Asp Asn Leu Leu Asn Ser Asp Asp Ile
    115                 120                 125
```

Asn Tyr Met Leu Asp Ala Leu Lys Ile Leu Gly Leu Asn Val Glu Thr
    130                 135                 140

His Ser Glu Asn Arg Ala Val Val Glu Gly Cys Gly Gly Val Phe
145                 150                 155                 160

Pro Ala Ser Ile Asp Ser Lys Ser Asp Ile Glu Leu Tyr Leu Gly Asn
                165                 170                 175

Ala Gly Thr Ala Met Arg Pro Leu Thr Ala Val Thr Ala Ala Gly
        180                 185                 190

Gly Asn Ala Ser Tyr Val Leu Asp Gly Val Pro Arg Met Arg Glu Arg
        195                 200                 205

Pro Ile Gly Asp Leu Val Val Gly Leu Lys Gln Leu Gly Ala Asp Val
210                 215                 220

Glu Cys Thr Leu Gly Thr Asn Cys Pro Pro Val Arg Val Asn Ala Asn
225                 230                 235                 240

Gly Gly Leu Pro Gly Gly Lys Val Lys Leu Ser Gly Ser Ile Ser Ser
                245                 250                 255

Gln Tyr Leu Thr Ala Leu Leu Met Ala Ala Pro Leu Ala Leu Gly Asp
        260                 265                 270

Val Glu Ile Glu Ile Val Asp Lys Leu Ile Ser Val Pro Tyr Val Glu
        275                 280                 285

Met Thr Leu Lys Leu Met Glu Arg Phe Gly Val Ser Ala Glu His Ser
290                 295                 300

Glu Ser Trp Asp Arg Phe Val Lys Gly Gln Lys Tyr Lys Ser
305                 310                 315                 320

Pro Gly Asn Ala Tyr Val Glu Gly Asp Ala Ser Ser Ala Ser Tyr Phe
                325                 330                 335

Leu Ala Gly Ala Ala Ile Thr Gly Glu Thr Val Thr Val Glu Gly Cys
        340                 345                 350

Gly Thr Thr Ser Leu Gln Gly Asp Val Lys Phe Ala Glu Val Leu Glu
        355                 360                 365

Lys Met Gly Cys Lys Val Ser Trp Thr Glu Asn Ser Val Thr Val Thr
370                 375                 380

Gly Pro Ser Arg Asp Ala Phe Gly Met Arg His Leu Arg Ala Ile Asp
385                 390                 395                 400

Val Asn Met Asn Lys Met Pro Asp Val Ala Met Thr Leu Ala Val Val
                405                 410                 415

Ala Leu Phe Ala Asp Gly Pro Thr Thr Ile Arg Asp Val Ala Ser Trp
        420                 425                 430

Arg Val Lys Glu Thr Glu Arg Met Ile Ala Ile Cys Thr Glu Leu Arg
        435                 440                 445

Lys Leu Gly Ala Thr Val Glu Glu Gly Ser Asp Tyr Cys Val Ile Thr
450                 455                 460

Pro Pro Lys Lys Val Lys Pro Ala Glu Ile Asp Thr Tyr Asp Asp His
465                 470                 475                 480

Arg Met Ala Met Ala Phe Ser Leu Ala Ala Cys Ala Asp Val Pro Ile
                485                 490                 495

Thr Ile Asn Asp Pro Gly Cys Thr Arg Lys Thr Phe Pro Asp Tyr Phe
        500                 505                 510

Gln Val Leu Glu Arg Ile Thr Lys His
        515                 520

<210> SEQ ID NO 20
<211> LENGTH: 514
<212> TYPE: PRT

<213> ORGANISM: Brassica sp.

<400> SEQUENCE: 20

```
Met Ala Gln Ala Ser Arg Ile Cys Gln Asn Pro Cys Val Ile Ser Asn
1               5                   10                  15
Leu Ser Lys Ser Asn Gln Arg Lys Ser Pro Phe Ser Val Ser Leu Lys
            20                  25                  30
Thr His Gln Gln Gln Arg Gly Ala Tyr Gln Ile Ser Ser Trp Gly Leu
        35                  40                  45
Lys Lys Ser Asn Asn Gly Ser Val Ile Arg Pro Val Lys Val Met Ala
    50                  55                  60
Ser Val Ser Thr Ala Glu Lys Ala Ser Glu Ile Val Leu Gln Pro Ile
65                  70                  75                  80
Arg Glu Ile Ser Gly Leu Ile Lys Leu Pro Gly Ser Lys Ser Leu Ser
                85                  90                  95
Asn Arg Ile Leu Leu Leu Ala Ala Leu Ser Glu Gly Thr Thr Val Val
            100                 105                 110
Asp Asn Leu Leu Asn Ser Asp Asp Ile Asn Tyr Met Leu Asp Ala Leu
        115                 120                 125
Asn Lys Leu Gly Leu Asn Val Glu Arg Asp Ser Glu Asn Asn Arg Ala
    130                 135                 140
Val Val Glu Gly Cys Gly Gly Ile Phe Pro Ala Ser Leu Asp Ser Lys
145                 150                 155                 160
Gly Asp Ile Glu Leu Tyr Leu Gly Asn Ala Gly Thr Ala Met Arg Pro
                165                 170                 175
Leu Thr Ala Ala Val Thr Ala Ala Gly Gly Asn Ala Ser Tyr Val Leu
            180                 185                 190
Asp Gly Val Pro Arg Met Arg Glu Arg Pro Ile Gly Asp Leu Val Val
        195                 200                 205
Gly Leu Lys Gln Leu Gly Ala Asp Val Glu Cys Thr Leu Gly Thr Asn
    210                 215                 220
Cys Pro Pro Val Arg Val Asn Ala Asn Gly Gly Leu Pro Gly Gly Lys
225                 230                 235                 240
Val Lys Leu Ser Gly Ser Ile Ser Ser Gln Tyr Leu Thr Ala Leu Leu
                245                 250                 255
Met Ala Ala Pro Leu Ala Leu Gly Asp Val Glu Ile Glu Ile Ile Asp
            260                 265                 270
Lys Leu Ile Ser Val Pro Tyr Val Glu Met Thr Leu Lys Leu Met Glu
        275                 280                 285
Arg Phe Gly Val Ser Ala Glu His Ser Asp Ser Trp Asp Arg Phe Phe
    290                 295                 300
Val Lys Gly Gly Gln Lys Tyr Lys Ser Pro Gly Asn Ala Tyr Val Glu
305                 310                 315                 320
Gly Asp Ala Ser Ala Ser Tyr Phe Leu Ala Gly Ala Ala Ile Thr
                325                 330                 335
Gly Glu Thr Val Thr Val Glu Gly Cys Gly Thr Thr Ser Leu Gln Gly
            340                 345                 350
Asp Val Lys Phe Ala Glu Val Leu Glu Lys Met Gly Cys Lys Val Ser
        355                 360                 365
Trp Thr Glu Asn Ser Val Thr Val Thr Gly Pro Ser Arg Asp Ala Phe
    370                 375                 380
Gly Met Arg His Leu Arg Ala Val Asp Val Asn Met Asn Lys Met Pro
385                 390                 395                 400
```

```
Asp Val Ala Met Thr Leu Ala Val Val Ala Leu Phe Ala Asp Gly Pro
                405                 410                 415

Thr Thr Ile Arg Asp Val Ala Ser Trp Arg Val Lys Glu Thr Glu Arg
            420                 425                 430

Met Ile Ala Ile Cys Thr Glu Leu Arg Lys Leu Gly Ala Thr Val Glu
        435                 440                 445

Glu Gly Ser Asp Tyr Cys Val Ile Thr Pro Ala Lys Leu Lys Pro
    450                 455                 460

Ala Glu Ile Asp Thr Tyr Asp Asp His Arg Met Ala Met Ala Phe Ser
465                 470                 475                 480

Leu Ala Ala Cys Ala Asp Val Pro Val Thr Ile Lys Asp Pro Gly Cys
                485                 490                 495

Thr Arg Lys Thr Phe Pro Asp Tyr Phe Gln Val Leu Glu Ser Ile Thr
            500                 505                 510

Lys His

<210> SEQ ID NO 21
<211> LENGTH: 516
<212> TYPE: PRT
<213> ORGANISM: Brassica sp.

<400> SEQUENCE: 21

Met Ala Gln Ser Ser Arg Ile Cys His Gly Val Gln Asn Pro Cys Val
1               5                   10                  15

Ile Ile Ser Asn Leu Ser Lys Ser Asn Gln Asn Lys Ser Pro Phe Ser
            20                  25                  30

Val Ser Leu Lys Thr His Gln Pro Arg Ala Ser Ser Trp Gly Leu Lys
        35                  40                  45

Lys Ser Gly Thr Met Leu Asn Gly Ser Val Ile Arg Pro Val Lys Val
    50                  55                  60

Thr Ala Ser Val Ser Thr Ser Glu Lys Ala Ser Glu Ile Val Leu Gln
65                  70                  75                  80

Pro Ile Arg Glu Ile Ser Gly Leu Ile Lys Leu Pro Gly Ser Lys Ser
                85                  90                  95

Leu Ser Asn Arg Ile Leu Leu Leu Ala Ala Leu Ser Glu Gly Thr Thr
            100                 105                 110

Val Val Asp Asn Leu Leu Asn Ser Asp Asp Ile Asn Tyr Met Leu Asp
        115                 120                 125

Ala Leu Lys Lys Leu Gly Leu Asn Val Glu Arg Asp Ser Val Asn Asn
    130                 135                 140

Arg Ala Val Val Glu Gly Cys Gly Gly Ile Phe Pro Ala Ser Leu Asp
145                 150                 155                 160

Ser Lys Ser Asp Ile Glu Leu Tyr Leu Gly Asn Ala Gly Thr Ala Met
                165                 170                 175

Arg Pro Leu Thr Ala Ala Val Thr Ala Ala Gly Gly Asn Ala Ser Tyr
            180                 185                 190

Val Leu Asp Gly Val Pro Arg Met Arg Glu Arg Pro Ile Gly Asp Leu
        195                 200                 205

Val Val Gly Leu Lys Gln Leu Gly Ala Asp Val Glu Cys Thr Leu Gly
    210                 215                 220

Thr Asn Cys Pro Pro Val Arg Val Asn Ala Asn Gly Gly Leu Pro Gly
225                 230                 235                 240

Gly Lys Val Lys Leu Ser Gly Ser Ile Ser Ser Gln Tyr Leu Thr Ala
                245                 250                 255
```

```
Leu Leu Met Ala Ala Pro Leu Ala Leu Gly Asp Val Glu Ile Glu Ile
            260             265             270

Ile Asp Lys Leu Ile Ser Val Pro Tyr Val Glu Met Thr Leu Lys Leu
        275             280             285

Met Glu Arg Phe Gly Val Ser Ala Glu His Ser Asp Ser Trp Asp Arg
        290             295             300

Phe Phe Val Lys Gly Gly Gln Lys Tyr Lys Ser Pro Gly Asn Ala Tyr
305         310             315             320

Val Glu Gly Asp Ala Ser Ser Ala Ser Tyr Phe Leu Ala Gly Ala Ala
            325             330             335

Ile Thr Gly Glu Thr Val Thr Val Glu Gly Cys Gly Thr Thr Ser Leu
            340             345             350

Gln Gly Asp Val Lys Phe Ala Glu Val Leu Glu Lys Met Gly Cys Lys
        355             360             365

Val Ser Trp Thr Glu Asn Ser Val Thr Val Thr Gly Pro Ser Arg Asp
    370             375             380

Ala Phe Gly Met Arg His Leu Arg Ala Val Asp Val Asn Met Asn Lys
385         390             395             400

Met Pro Asp Val Ala Met Thr Leu Ala Val Val Ala Leu Phe Ala Asp
            405             410             415

Gly Pro Thr Thr Ile Arg Asp Val Ala Ser Trp Arg Val Lys Glu Thr
            420             425             430

Glu Arg Met Ile Ala Ile Cys Thr Glu Leu Arg Lys Leu Gly Ala Thr
        435             440             445

Val Glu Glu Gly Ser Asp Tyr Cys Val Ile Thr Pro Pro Ala Lys Val
    450             455             460

Lys Pro Ala Glu Ile Asp Thr Tyr Asp Asp His Arg Met Ala Met Ala
465             470             475             480

Phe Ser Leu Ala Ala Cys Ala Asp Val Pro Val Thr Ile Lys Asp Pro
            485             490             495

Gly Cys Thr Arg Lys Thr Phe Pro Asp Tyr Phe Gln Val Leu Glu Ser
            500             505             510

Ile Thr Lys His
        515
```

EPSPS MUTANTS

CROSS-REFERENCE TO RELATED APPLICATION

This application is a continuation of U.S. patent application Ser. No. 13/621,662, filed Sep. 17, 2012, which is a divisional of U.S. patent application Ser. No. 12/160,725, filed Nov. 17, 2008, now U.S. Pat. No. 8,268,622, issued Sep. 18, 2012, which is the national stage application of International Application No. PCT/US2007/000591, filed Jan. 10, 2007, which claims the benefit of U.S. Provisional Application No. 60/758,439, filed Jan. 12, 2006, all of which are hereby incorporated by reference herein in their entirety, including any figures, tables, or drawings.

SEQUENCE LISTING

The instant application contains a Sequence Listing which has been submitted in ASCII format via EFS-Web and is hereby incorporated by reference in its entirety. Said ASCII copy, created on Jul. 19, 2018, is named CIBUS-007-CT_SeqListing.txt and is 25 kilobytes in size.

FIELD OF THE INVENTION

The present invention relates to the production of a non-transgenic plant resistant or tolerant to an herbicide of the phosphonomethylglycine family, e.g., glyphosate. The present invention also relates to the use of a recombinagenic oligonucleobase to make a desired mutation in the chromosomal or episomal sequences of a plant in the gene encoding for 5-enol pyruvylshikimate-3-phosphate synthase (EPSPS). The mutated protein, which substantially maintains the catalytic activity of the wild-type protein, allows for increased resistance or tolerance of the plant to a herbicide of the phosphonomethylglycine family, and allows for the substantially normal growth or development of the plant, its organs, tissues or cells as compared to the wild-type plant regardless of the presence or absence of the herbicide. The present invention also relates to an *E. coli* cell having a mutated EPSPS gene, a non-transgenic plant cell in which the EPSPS gene has been mutated, a non-transgenic plant regenerated therefrom, as well as a plant resulting from a cross using a regenerated non-transgenic plant having a mutated EPSPS gene as one of the parents of the cross. The present mutated EPSPS protein has been changed in amino acid positions 159, 178, 182, 193, 244, 273 and/or 454 in the *Arabidopsis* EPSPS protein (NM 130093) or at an analogous amino acid residue in an EPSPS paralog.

BACKGROUND OF THE INVENTION

Phosphonomethylglycine Herbicides

Herbicide-tolerant plants may reduce the need for tillage to control weeds thereby effectively reducing soil erosion. One herbicide which is the subject of much investigation in this regard is N-phosphonomethylglycine, commonly referred to as glyphosate. Glyphosate inhibits the shikimic acid pathway which leads to the biosynthesis of aromatic compounds including amino acids, hormones and vitamins. Specifically, glyphosate curbs the conversion of phosphoenolpyruvic acid (PEP) and 3-phosphoshikimic acid to 5-enolpyruvyL-3-phosphoshikimic acid by inhibiting the enzyme 5-enolpyruvylshikimate-3-phosphate synthase (hereinafter referred to as EPSP synthase or EPSPS). For purposes of the present invention, the term "glyphosate" includes any herbicidally effective form of N-phosphonomethylglycine (including any salt thereof), other forms which result in the production of the glyphosate anion in plants and any other herbicides of the phosphonomethlyglycine family.

Tolerance of plants to glyphosate can be increased by introducing a mutant EPSPS gene having an alteration in the EPSPS amino acid coding sequence into the genome of the plant. Examples of some of the mutations in the EPSPS gene for inducing glyphosate tolerance are described in the following patents: U.S. Pat. Nos. 5,310,667; 5,866,775; 5,312,910; 5,145,783. These proposed mutations typically have a higher $K_I$ for glyphosate than the wild-type EPSPS enzyme which confers the glyphosate-tolerant phenotype, but these variants are also characterized by a high $K_m$ for PEP which makes the enzyme kinetically less efficient (Kishore et al., 1998, Ann. Rev. Biochem. 57:627-663; Schulz et al., 1984, Arch. Microbiol. 137:121-123; Sost et al., 1984, FEBS Lett. 173:238-241; Kishore et al., 1986, Fed. Proc. 45: 1506; Sost and Amrhein, 1990, Arch. Biochem. Biophys. 282: 433-436). Many mutations of the EPSPS gene are chosen so as to produce an EPSPS enzyme that is resistant to herbicides, but unfortunately, the EPSPS enzyme produced by the mutated EPSPS gene has a significantly lower enzymatic activity than the wild-type EPSPS. For example, the apparent $K_m$ for PEP and the apparent $K_I$ for glyphosate for the wild-type EPSPS from *E. coli* are 10 µM and 0.5 µM, respectively, while for a glyphosate-tolerant isolate having a single amino acid substitution of alanine for glycine at position 96, these values are 220 µM and 4.0 mM, respectively. A number of glyphosate-tolerant EPSPS genes have been constructed by mutagenesis. Again, the glyphosate-tolerant EPSPS had lower catalytic efficiency ($V_{max}/K_m$), as shown by an increase in the $K_m$ for PEP, and a slight reduction of the $V_{max}$ of the wild-type plant enzyme (Kishore et al., 1998, Ann. Rev. Biochem. 57:627-663).

Since the kinetic constants of the variant enzymes are impaired with respect to PEP, it has been proposed that high levels of overproduction of the variant enzyme, 40-80 fold, would be required to maintain normal catalytic activity in plants in the presence of glyphosate (Kishore et al., 1988, Ann. Rev. Biochem. 57:627-663). It has been shown that glyphosate-tolerant plants can be produced by inserting into the genome of the plant the capacity to produce a higher level of EPSP synthase in the chloroplast of the cell (Shah et al., 1986, Science 233, 478-481), which enzyme is preferably glyphosate-tolerant (Kishore et al., 1988, Ann. Rev. Biochem. 57:627-663).

The introduction of the exogenous mutant EPSPS genes into plant is well documented. For example, according to U.S. Pat. No. 4,545,060, to increase a plant's resistance to glyphosate, a gene coding for an EPSPS variant having at least one mutation that renders the enzyme more resistant to its competitive inhibitor, i.e., glyphosate, is introduced into the plant genome. However, many complications and problems are associated with these transgenic plants containing mutant EPSPS genes. Many such mutations result in low expression of the mutated EPSPS gene product or result in an EPSPS gene product with significantly lower enzymatic activity as compared to wild type. The low expression or low enzymatic activity of the mutated enzyme results in abnormally low levels of growth and development of the plant.

While such variants in the EPSP synthases have proved useful in obtaining transgenic plants tolerant to glyphosate, it would be increasingly beneficial to obtain a variant EPSPS gene product that is highly glyphosate-tolerant but still kinetically efficient, such that improved tolerance can be obtained with a wild-type expression level.

Recombinagenic Oligonucleobases

Recombinagenic oligonucleobases and their use to effect genetic changes in eukaryotic cells are described in U.S. Pat. No. 5,565,350 to Kmiec (Kmiec I). Kmiec I teaches a method for introducing specific genetic alterations into a target gene. Kmiec I discloses, inter alia, recombinagenic oligonucleobases having two strands, in which a first strand contains two segments of at least 8 RNA-like nucleotides that are separated by a third segment of from 4 to about 50 DNA-like nucleotides, termed an "interposed DNA segment." The nucleotides of the first strand are base paired to DNA-like nucleotides of a second strand. The first and second strands are additionally linked by a segment of single stranded nucleotides so that the first and second strands are parts of a single oligonucleotide chain. Kmiec I further teaches a method for introducing specific genetic alterations into a target gene. According to Kmiec I, the sequences of the RNA segments are selected to be homologous, i.e., identical, to the sequence of a first and a second fragment of the target gene. The sequence of the interposed DNA segment is homologous with the sequence of the target gene between the first and second fragment except for a region of difference, termed the "heterologous region." The heterologous region can effect an insertion or deletion, or can contain one or more bases that are mismatched with the sequence of target gene so as to effect a substitution. According to Kmiec I, the sequence of the target gene is altered as directed by the heterologous region, such that the target gene becomes homologous with the sequence of the recombinagenic oligonucleobase. Kmiec I specifically teaches that ribose and 2'-O-methylribose, i.e., 2'-methoxyribose, containing nucleotides can be used in recombinagenic oligonucleobases and that naturally-occurring deoxyribose-containing nucleotides can be used as DNA-like nucleotides.

U.S. Pat. No. 5,731,181 to Kmiec (Kmiec II) specifically disclose the use of recombinagenic oligonucleobases to effect genetic changes in plant cells and discloses further examples of analogs and derivatives of RNA-like and DNA-like nucleotides that can be used to effect genetic changes in specific target genes. Other patents discussing the use of recombinagenic oligonucleobases include: U.S. Pat. Nos. 5,756,325; 5,871,984; 5,760,012; 5,888,983; 5,795,972; 5,780,296; 5,945,339; 6,004,804; and 6,010,907 and in International Patent No. PCT/US00/23457; and in International Patent Publication Nos. WO 98/49350; WO 99/07865; WO 99/58723; WO 99/58702; and WO 99/40789. Recombinagenic oligonucleobases include mixed duplex oligonucleotides, non-nucleotide containing molecules taught in Kmiec II and other molecules taught in the above-noted patents and patent publications.

U.S. Pat. No. 6,870,075 ('075 patent) discloses a method for producing a non-transgenic, herbicide resistant or tolerant plants employing recombinagenic oligonucleobases according to the methods disclosed in Kmiec I and Kmiec II. The EPSPS mutants disclosed in the '075 patent include changes made in the following amino acid positions of the EPSPS protein: $Leu_{173}$, $Gly_{177}$, $Thr_{178}$, $Ala_{179}$, $Met_{180}$, $Arg_{181}$, $Pro_{182}$, $Ser_{98}$, $Ser_{255}$ and $Leu_{198}$ in the *Arabidopsis* EPSPS protein or at an analogous amino acid residue in an EPSPS paralog.

Published US Patent Application 20030084473 also discloses the use of recombinagenic oligonucleobases to make non-transgenic herbicide resistant plants where the EPSPS protein has been changed in amino acid positions 126, 177, 207, 438, 479, 480 and/or 505 in the *Arabidopsis* EPSPS protein or at an analogous amino acid residue in an EPSPS paralog.

The present invention relates to additional amino acid mutations that can be made in any EPSPS gene from any species to produce a gene product that possesses resistance to glyphosate.

SUMMARY OF THE INVENTION

Briefly, in accordance with the present invention, a non-transgenic plant or plant cell having one or more mutations in the EPSPS gene is made. The resulting plant has increased resistance or tolerance to a member of the phosphonomethylglycine family such as glyphosate and exhibits substantially normal growth or development of the plant, its organs, tissues or cells, as compared to the corresponding wild-type plant or cell. The mutated gene produces a gene product having a substitution at one or more of the amino acid positions 160, 179, 183, 194, 244, 273 and/or 454 in the *Arabidopsis* EPSPS protein (AF360224) or at an analogous amino acid residue in an EPSPS paralog. Preferably, the mutated plant is resistant to glyphosate and has substantially the same catalytic activity as compared to the wild-type EPSPS protein.

Additionally, the present invention includes a mutated EPSPS gene from an *E coli* and mutated *E coli* cells that produces a gene product having a substitution at one or more of the amino acid positions 82, 97, 101, 114, 164, 193 and 374. The mutated *E coli* EPSPS gene can be used for in vitro testing of the mutated gene product. Once active *E coli* mutants have been identified then corresponding mutants can then be made to an EPSPS gene in a desirable crop to impart herbicide resistance to the crop.

The present invention also relates to a method for producing a non-transgenic plant having a mutated EPSPS gene that substantially maintains the catalytic activity of the wild-type protein regardless of the presence or absence of a herbicide of the phosphonomethylglycine family. The method comprises introducing into a plant cell a recombinagenic oligonucleobase with a targeted mutation in the EPSPS gene that produces a gene product having one or more of the aforementioned amino acid changes. The method further includes identifying a cell, seed, or plant having a mutated EPSPS gene and to culturing and regeneration methods to obtain a plant that produces seeds, henceforth a "fertile plant", and the production of seeds and additional plants from such a fertile plant including descendant (progeny) plants that contain the mutated EPSPS gene.

The invention is further directed to a method of selectively controlling weeds in a field. The field comprises plants with the disclosed EPSPS gene alterations and weeds. The method comprises application to the field of a phospnomethyglycine herbicide to which the said plants are rendered resistant and the weeds are controlled. A preferred herbicide is glyphosate.

The invention is also directed to novel mutations in the EPSPS gene and resulting novel gene product that confer resistance or tolerance to a member of the phosphonomethylglycine family, e.g., glyphosate, to a plant or wherein the mutated EPSPS has substantially the same enzymatic activity as compared to wild-type EPSPS. Additionally, the present invention is directed to a mutated *E. coli* EPSPS gene product (protein) that is used to screen EPSPS mutants for use as herbicide resistant mutations in plants.

BRIEF DESCRIPTION OF THE DRAWINGS

FIG. 1 shows the EPSPS gene (AroA gene) product protein sequence (SEQ ID NO: 17) in *E. Coli* where the mutated amino acid positions are depicted with a box around them. The substituted amino acid in those positions is shown below the sequence.

FIG. 2 shows the protein sequence (SEQ ID NO: 18) of AtEPSPS cDNA-At2g45300 translated from Genbank accession NM_130093 (Arabodopsis).

FIG. 3 shows the protein sequence (SEQ ID NO: 19) of AtEPSPS cDNA-At1g48860 translated from Genbank accession AF360224T (Arabodopsis).

FIG. 4 shows the protein sequence (SEQ ID NO: 20) of BnEPSPS cDNA-BN-2 2-23 (Canola).

FIG. 5 shows the protein sequence (SEQ ID NO: 21) of BnEPSPS cDNA-2-28 from X51475 gDNA translation (Canola).

DETAILED DESCRIPTION OF THE INVENTION

Definitions

The invention is to be understood in accordance with the following definitions.

An oligonucleobase is a polymer of nucleobases, which polymer can hybridize by Watson-Crick base pairing to a DNA having the complementary sequence.

Nucleobases comprise a base, which is a purine, pyrimidine, or a derivative or analog thereof. Nucleobases include peptide nucleobases, the subunits of peptide nucleic acids, and morpholine nucleobases as well as nucleosides and nucleotides. Nucleosides are nucleobases that contain a pentosefuranosyl moiety, e.g., an optionally substituted riboside or 2'-deoxyriboside. Nucleosides can be linked by one of several linkage moieties, which may or may not contain a phosphorus. Nucleosides that are linked by unsubstituted phosphodiester linkages are termed nucleotides.

An oligonucleobase chain has a single 5' and 3' terminus, which are the ultimate nucleobases of the polymer. A particular oligonucleobase chain can contain nucleobases of all types. An oligonucleobase compound is a compound comprising one or more oligonucleobase chains that are complementary and hybridized by Watson-Crick base pairing. Nucleobases are either deoxyribo-type or ribo-type. Ribo-type nucleobases are pentosefuranosyl containing nucleobases wherein the 2' carbon is a methylene substituted with a hydroxyl, alkyloxy or halogen. Deoxyribo-type nucleobases are nucleobases other than ribo-type nucleobases and include all nucleobases that do not contain a pentosefuranosyl moiety.

An oligonucleobase strand generically includes both oligonucleobase chains and segments or regions of oligonucleobase chains. An oligonucleobase strand has a 3' end and a 5' end. When a oligonucleobase strand is coextensive with a chain, the 3' and 5' ends of the strand are also 3' and 5' termini of the chain.

According to the present invention, substantially normal growth of a plant, plant organ, plant tissue or plant cell is defined as a growth rate or rate of cell division of the plant, plant organ, plant tissue, or plant cell that is at least 35%, at least 50%, at least 60%, or at least 75% of the growth rate or rate of cell division in a corresponding plant, plant organ, plant tissue or plant cell expressing the wild type EPSPS protein.

According to the present invention, substantially normal development of a plant, plant organ, plant tissue or plant cell is defined as the occurrence of one or more developmental events in the plant, plant organ, plant tissue or plant cell that are substantially the same as those occurring in a corresponding plant, plant organ, plant tissue or plant cell expressing the wild type EPSPS protein.

According to the present invention plant organs include, but are not limited to, leaves, stems, roots, vegetative buds, floral buds, meristems, embryos, cotyledons, endosperm, sepals, petals, pistils, carpels, stamens, anthers, microspores, pollen, pollen tubes, ovules, ovaries and fruits, or sections, slices or discs taken therefrom. Plant tissues include, but are not limited to, callus tissues, ground tissues, vascular tissues, storage tissues, meristematic tissues, leaf tissues, shoot tissues, root tissues, gall tissues, plant tumor tissues, and reproductive tissues. Plant cells include, but are not limited to, isolated cells with cell walls, variously sized aggregates thereof, and protoplasts.

Plants are substantially "tolerant" to glyphosate when they are subjected to it and provide a dose/response curve which is shifted to the right when compared with that provided by similarly subjected non-tolerant like plant. Such dose/response curves have "dose" plotted on the X-axis and "percentage kill", "herbicidal effect", etc., plotted on the y-axis. Tolerant plants will require more herbicide than non-tolerant like plants in order to produce a given herbicidal effect. Plants which are substantially "resistant" to the glyphosate exhibit few, if any, necrotic, lytic, chlorotic or other lesions, when subjected to glyphosate at concentrations and rates which are typically employed by the agrochemical community to kill weeds in the field. Plants which are resistant to a herbicide are also tolerant of the herbicide. The terms "resistant" and "tolerant" are to be construed as "tolerant and/or resistant" within the context of the present application.

The term "EPSPS homolog" or any variation therefore refers to an EPSPS gene or EPSPS gene product found in another plant species that performs the same or substantially the same biological function as the EPSPS genes disclosed herein and where the nucleic acid sequences or polypeptide sequences (of the EPSPS gene product) are said to be "identical" or at least 50% similar (also referred to as 'percent identity' or 'substantially identical') as described below. Two polynucleotides or polypeptides are identical if the sequence of nucleotides or amino acid residues, respectively, in the two sequences is the same when aligned for maximum correspondence as described below. The terms "identical" or "percent identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. For polypeptides where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a 'score of zero, a conservative substitution is given a score between zero and 1. The scoring of conservative substitutions is calculated according to, e.g., the algorithm of Meyers & Miller, Computer Applic. Biol. Sci. 4: 11-17 (1988) e.g., as implemented in the program PC/GENE (Intelligenetics, Mountain View, Calif., USA).

The phrases "substantially identical," and "percent identity" in the context of two nucleic acids or polypeptides, refer to sequences or subsequences that have at least 50%, advantageously 60%, preferably 70%, more preferably 80%, and most preferably 90-95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

One of skill in the art will recognize that two polypeptides can also be "substantially identical" if the two polypeptides are immunologically similar. Thus, overall protein structure may be similar while the primary structure of the two polypeptides display significant variation. Therefore a method to measure whether two polypeptides are substantially identical involves measuring the binding of monoclonal or polyclonal antibodies to each polypeptide. Two polypeptides are substantially identical if the antibodies specific for a first polypeptide bind to a second polypeptide with an affinity of at least one third of the affinity for the first polypeptide. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, 0.4dv. Appl. Math. 2:482 (I 98 I), by the homology alignment algorithm of Needleman & Wunsch, J. Mol. Biol. 48:443 (1970), by the search for similarity method of Pearson & Lipman, Proc. Nat'l. Acad. Sci. USA 5 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), by software for alignments such as VECTOR NTI Version #6 by InforMax, Inc. MD, USA, by the procedures described in ClustalW, Thompson, J. D., Higgins, D. G. and Gibson, T. J. (1994) CLUSTALW: improving the sensitivity of progressive multiple sequence alignment through sequence weighting, position—specific gap penalties and weight matrix choice. Nucleic Acids Research, 22:4673-4680 or by visual inspection (see generally, Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1977) Nucleic Acids Res. 25: 33 89-3402, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff& Henikoff, Proc. Natl. Acad. Sci. USA 89:10915 (1989)). In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

In practicing the present invention a non-transgenic plant or plant cell having one or more mutations in the EPSPS gene is made. The resulting plant has increased resistance or tolerance to a member of the phosphonomethylglycine family such as glyphosate and exhibits substantially normal growth or development of the plant, its organs, tissues or cells, as compared to the corresponding wild-type plant or cell. The mutated gene produces a gene product having a substitution at one or more of the amino acid positions 160, 179, 183, 194, 244, 273 and 454 of the *Arabidopsis* EPSPS gene AF 360244 product or at an analogous amino acid position in an EPSPS homolog. Preferably, the mutated plant is resistant to glyphosate and has substantially the same catalytic activity as compared to the wild-type EPSPS protein.

To identify mutant EPSPS genes that will produce a gene product that provides resistance to glyphosate, in vitro screening can be done in a bacterial system to save time and resources. Growth curves of bacterial colonies expressing candidate mutant EPSPS genes can be generated to evaluate the mutant EPSPS genes in providing a glyphosate resistant phenotype. For example, U.S. Pat. No. 6,870,075 discloses a *Salmonella* glyphosate resistance assay employing *Arabidopsis* mutant EPSPS genes transformed into a LacZ-*Salmonella typhi* strain. In another embodiment of the present invention, the *E coli* EPSPS gene, also called the AroA gene, can be used to evaluate EPSPS mutants for glyphosate resistance. Growth curve assays and enzymatic assays measuring $K_i$ and $K_m$ values for candidate mutants are conducted according to well known assay techniques. Once an active glyphosate resistant mutant is identified in *E coli* EPSPS gene then an analogous amino acid in a plant EPSPS gene is mutated with recombinagenic nucleobases as described herein to make a glyphosate resistant plant.

Preferred amino acid substitutions in the *E. coli* EPSPS gene (AroA) product include the following:
Leu$_{82}$Ser
Thr$_{97}$Ile or Ala
Pro$_{101}$Ala or Thr or Leu or Cys or Gly
Val$_{114}$Ala
Asp$_{164}$Ala
Asn$_{193}$Ala and
X$_{374}$LeU
wherein the amino acid to the left of the subscript number is the native amino acid and the amino acid to the right of the subscript number is the mutant amino acid. The letter "X" in amino acid position 374 is designated because in the *E. coli* EPSPS gene product the native amino acid is Leu. However, it has been discovered that in many plant species the amino acid present in position 374 is not Leu and when this position is changed to Leu the plant will exhibit glyphosate resistance and will retain sufficient enzymatic activity to support normal plant growth.

Corresponding amino acid positions in plant species are changed according to the present invention to produce a non-transgenic herbicide resistant plant. Below is a list of some preferred crops which list the amino acid positions in the EPSPS gene to be changed. Preferred amino acid substitutions are listed to the right of the amino acid position number.

For maize the following amino acid changes are preferred:
Leu$_{84}$Ser
Thr$_{102}$Ile or Ala
Pro$_{106}$Ala or Thr or Leu or Cys or Gly
Val$_{114}$Ala
Asp$_{164}$Ala
Asn$_{193}$Ala and
X$_{117}$Leu For cotton the following amino acid changes are preferred:
Leu$_{82}$Ser
Thr$_{97}$Ile or Ala
Pro$_{173}$Ala or Thr or Leu or Cys or Gly
Val$_{114}$Ala
Asp$_{164}$Ala
Asn$_{193}$Ala and
X$_{184}$Leu For rice the following amino acid changes are preferred
Leu$_{150}$Ser
Thr$_{169}$Ile or Ala
Pro$_{173}$Ala or Thr or Leu or Cys or Gly
Val$_{114}$Ala
Asp$_{164}$Ala
Asn$_{193}$Ala and
X$_{184}$Leu For *Brassica napus* (2-28 from X51475 gDNA translation) the following amino acid changes are preferred:
Leu$_{155}$Ser
Thr$_{174}$Ile or Ala
Pro$_{178}$Ala or Thr or Leu or Cys or Gly
Val$_{114}$Ala
Asp$_{164}$Ala
Asn$_{193}$Ala and
X$_{189}$Leu For *Arabidopsis thaliana* (AF360224) the following amino acid changes are preferred:
Leu$_{160}$Ser
Thr$_{179}$Ile or Ala
Pro$_{183}$Ala or Thr or Leu or Cys or Gly
Val$_{114}$Ala
Asp$_{164}$Ala
Asn$_{193}$Ala and
X$_{194}$Leu For *Petunia hybrida* the following amino acid changes are preferred:
Leu$_{155}$Ser
Thr$_{174}$Ile or Ala
Pro$_{178}$Ala or Thr or Leu or Cys or Gly
Val$_{114}$Ala
Asp$_{164}$Ala
Asn$_{193}$Ala and
X$_{189}$Leu As will be appreciated, *E. coli* is not a plant however it is contemplated in the present invention because the *E. coli* gene can be mutated in a bacterial cell culture system and then the mutated *E. coli* gene product (enzyme) can be assayed for enzymatic activity ($K_i$ and $K_m$) that will indicate resistance to glyphosate and function as a necessary enzyme product which is essential in plants. Once a mutated *E. coli* mutant is identified then that mutation is made in a plant cell employing the recombinagenic oligonucleobases described herein to produce a non-transgenic herbicide resistant plant. For these reasons mutated *E coli* and mutated Area proteins are considered part of the present invention.

The following table lists preferred amino acid substitution positions, by amino acid number, for various species. Making amino acid substitutions at one or more of these positions will produce glyphosate resistant plants:

| Protein | Genbank Accession # | L82 | T97 | P101 | N111 |
|---|---|---|---|---|---|
| *E. coli* | X00557 | 82 | 97 | 101 | 111* |
| *Arabidopsis thaliana* | AF360224 | 160 | 179 | 183 | 194 |
| *Petunia hybrida* | M21084.1 | 155 | 174 | 178 | 189 |
| *Brassica napus* | X51475.1 | 155 | 174 | 178 | 189 |
| *Zea mays* | X63374 | 84 | 102 | 106 | 117 |
| *Oryza sativa* | AF413082 | 150 | 169 | 173 | 184 |
| *Arabidopsis thaliana* | NM 130093 | 159 | 178 | 182 | 193 |

*No true *E. coli* homologous amino acid

As can be seen from the above table and FIG. 1-5 there are some minor variations among the EPSPS genes between species and within species. This is to be expected. These minor variations should be taken into account when making mutants according to the present invention. Amino acids in analogous positions between the different genes are mutated to make glyphosate resistant plants. For example, the mutation in *Arabidopsis* AF360224 at position 179 (T>A) would be equivalent to a T>A mutation at position 178 in *Arabidopsis* NM 130093. Another example is seen in position L82 in the *E coli* EPSPS gene. Most plants have an L in the analgous position but *Arabidopsis* has an F the analogous at 159 or 160 depending on the *Arabidopsis* gene as indicated in the above table.

Additionally, some species have more than one EPSPS gene. In such a case one or more of the genes are mutated according to the present invention to make a glyphosate resistant mutant. If the expression levels of the various EPSPS genes is known and is different then it is preferred to mutate the higher expressing EPSPS genes. In a preferred embodiment all of the EPSPS genes in a crop are mutated to make a glyphosate phenotype. For example, canola is known to have four EPSPS genes. Two genes are shown in FIGS. 4 and 5. A comparison will show a light difference between the two genes.

The plant mutated according to the present invention can be of any species of dicotyledonous, monocotyledonous or gymnospermous plant, including any woody plant species that grows as a tree or shrub, any herbaceous species, or any species that produces edible fruits, seeds or vegetables, or any species that produces colorful or aromatic flowers. For example, the plant may be selected from a species of plant from the group consisting of canola, sunflower, tobacco, sugar beet, sweet potato, yam, cotton, maize, wheat, barley, rice, sorghum, tomato, mango, peach, apple, pear, strawberry, banana, melon, potato, carrot, lettuce, onion, soya spp, sugar cane, pea, peanut, field beans, poplar, grape, citrus, alfalfa, rye, oats, turf and forage grasses, flax, oilseed rape, cucumber, morning glory, balsam, pepper, eggplant, marigold, lotus, cabbage, daisy, carnation, tulip, iris, lily, and nut producing plants insofar as they are not already specifically mentioned.

The recombinagenic oligonucleobase can be introduced into a plant cell using any method commonly used in the art, including but not limited to, microcarriers (biolistic delivery), microfibers (whiskers), electroporation, direct DNA uptake and microinjection.

Illustrative examples of a recombinagenic oligonucleobase are described below.

The invention can be practiced with recombinagenic oligonucleobases having the conformations and chemistries described in the Kmiec I and Kmiec II patents which are incorporated herein by reference. Kmiec I teaches a method for introducing specific genetic alterations into a target gene. The recombinagenic oligonucleobases in Kmiec I and/or Kmiec II contain two complementary strands, one of which contains at least one segment of RNA-type nucleotides (an "RNA segment") that are base paired to DNA-type nucleotides of the other strand.

Kmiec II discloses that purine and pyrimidine base-containing non-nucleotides can be substituted for nucleotides. U.S. Pat. Nos. 5,756,325; 5,871,984; 5,760,012; 5,888,983; 5,795,972; 5,780,296; 5,945,339; 6,004,804; and 6,010,907 and in International Patent No. PCT/US00/23457; and in International Patent Publication Nos. WO 98/49350; WO 99/07865; WO 99/58723; WO 99/58702; WO 99/40789; U.S. Pat. No. 6,870,075; and US Published Patent Application 20030084473, which are each hereby incorporated in their entirety, disclose additional recombinagenic molecules that can be used for the present invention. The term "recombinagenic oligonucleobase" is used herein to denote the molecules that can be used in the methods of the present invention and include mixed duplex oligonucleotides, non-nucleotide containing molecules taught in Kmiec II, single stranded oligodeoxynucleotides and other recombinagenic molecules taught in the above noted patents and patent publications.

In one embodiment, the recombinagenic oligonucleobase is a mixed duplex oligonucleotide in which the RNA-type nucleotides of the mixed duplex oligonucleotide are made RNase resistant by replacing the 2'-hydroxyl with a fluoro, chloro or bromo functionality or by placing a substituent on the 2'-O. Suitable substituents include the substituents taught by the Kmiec II. Alternative substituents include the substituents taught by U.S. Pat. No. 5,334,711 (Sproat) and the substituents taught by patent publications EP 629 387 and EP 679 657 (collectively, the Martin Applications), which are incorporated herein by reference. As used herein, a 2'-fluoro, chloro or bromo derivative of a ribonucleotide or a ribonucleotide having a 2'-OH substituted with a substituent described in the Martin Applications or Sproat is termed a "2'-Substituted Ribonucleotide." As used herein the term "RNA-type nucleotide" means a 2'-hydroxyl or 2'-Substituted Nucleotide that is linked to other nucleotides of a mixed duplex oligonucleotide by an unsubstituted phosphodiester linkage or any of the non-natural linkages taught by Kmiec I or Kmiec II. As used herein the term "deoxyribo-type nucleotide" means a nucleotide having a 2'-H, which can be linked to other nucleotides of a MDON by an unsubstituted phosphodiester linkage or any of the non-natural linkages taught by Kmiec I or Kmiec II.

In one embodiment of the present invention, the recombinagenic oligonucleobase is a mixed duplex oligonucleotide that is linked solely by unsubstituted phosphodiester bonds. In alternative embodiments, the linkage is by substituted phosphodiesters, phosphodiester derivatives and non-phosphorus-based linkages as taught by Kmiec II. In yet another embodiment, each RNA-type nucleotide in the mixed duplex oligonucleotide is a 2'-Substituted Nucleotide. Particularly preferred embodiments of 2'-Substituted Ribonucleotides are 2'-fluoro, 2'-methoxy, 2'-propyloxy, 2'-allyloxy, 2'-hydroxylethyloxy, 2'-methoxyethyloxy, 2'-fluoropropyloxy and 2'-trifluoropropyloxy substituted ribonucleotides. More preferred embodiments of 2'-Substituted Ribonucleotides are 2'-fluoro, 2'-methoxy, 2'-methoxyethyloxy, and 2'-allyloxy substituted nucleotides. In another embodiment the mixed duplex oligonucleotide is linked by unsubstituted phosphodiester bonds.

Although mixed duplex oligonucleotide having only a single type of 2'-substituted RNA-type nucleotide are more conveniently synthesized, the methods of the invention can be practiced with mixed duplex oligonucleotides having two or more types of RNA-type nucleotides. The function of an RNA segment may not be affected by an interruption caused by the introduction of a deoxynucleotide between two RNA-type trinucleotides, accordingly, the term RNA segment encompasses such an "interrupted RNA segment." An uninterrupted RNA segment is termed a contiguous RNA segment. In an alternative embodiment an RNA segment can contain alternating RNase-resistant and unsubstituted 2'-OH nucleotides. The mixed duplex oligonucleotides preferably have fewer than 100 nucleotides and more preferably fewer than 85 nucleotides, but more than 50 nucleotides. The first and second strands are Watson-Crick base paired. In one embodiment the strands of the mixed duplex oligonucleotide are covalently bonded by a linker, such as a single stranded hexa, penta or tetranucleotide so that the first and second strands are segments of a single oligonucleotide chain having a single 3' and a single 5' end. The 3' and 5' ends can be protected by the addition of a "hairpin cap" whereby the 3' and 5' terminal nucleotides are Watson-Crick paired to adjacent nucleotides. A second hairpin cap can, additionally, be placed at the junction between the first and second strands distant from the 3' and 5' ends, so that the Watson-Crick pairing between the first and second strands is stabilized.

The first and second strands contain two regions that are homologous with two fragments of the target EPSPS gene, i.e., have the same sequence as the target gene. A homologous region contains the nucleotides of an RNA segment and may contain one or more DNA-type nucleotides of connecting DNA segment and may also contain DNA-type nucleotides that are not within the intervening DNA segment. The two regions of homology are separated by, and each is adjacent to, a region having a sequence that differs from the sequence of the target gene, termed a "heterologous region."

The heterologous region can contain one, two or three mismatched nucleotides. The mismatched nucleotides can be contiguous or alternatively can be separated by one or two nucleotides that are homologous with the target gene. Alternatively, the heterologous region can also contain an insertion or one, two, three or of five or fewer nucleotides. Alternatively, the sequence of the mixed duplex oligonucleotide may differ from the sequence of the target gene only by the deletion of one, two, three, or five or fewer nucleotides from the mixed duplex oligonucleotide. The length and position of the heterologous region is, in this case, deemed to be the length of the deletion, even though no nucleotides of the mixed duplex oligonucleotide are within the heterologous region. The distance between the fragments of the target gene that are complementary to the two homologous regions is identically the length of the heterologous region when a substitution or substitutions is intended. When the heterologous region contains an insertion, the homologous regions are thereby separated in the mixed duplex oligonucleotide farther than their complementary homologous fragments are in the gene, and the converse is applicable when the heterologous region encodes a deletion.

The RNA segments of the mixed duplex oligonucleotides are each a part of a homologous region, i.e., a region that is identical in sequence to a fragment of the target gene, which segments together preferably contain at least 13 RNA-type nucleotides and preferably from 16 to 25 RNA-type nucleotides or yet more preferably 18-22 RNA-type nucleotides or most preferably 20 nucleotides. In one embodiment, RNA segments of the homology regions are separated by and adjacent to, i.e., "connected by" an intervening DNA segment. In one embodiment, each nucleotide of the heterologous region is a nucleotide of the intervening DNA segment. An intervening DNA segment that contains the heterologous region of a mixed duplex oligonucleotide is termed a "mutator segment."

The change to be introduced into the target EPSPS gene is encoded by the heterologous region. The change to be introduced into the EPSPS gene may be a change in one or more bases of the EPSPS gene sequence that changes the native amino acid in that position to the desired amino acid.

In another embodiment of the present invention, the recombinagenic oligonucleobase is a single stranded oligodeoxynucleotide mutational vector or SSOMV, which is disclosed in International Patent Application PCT/US00/23457, which is incorporated herein by reference in its entirety. The sequence of the SSOMV is based on the same principles as the mutational vectors described in U.S. Pat. Nos. 5,756,325; 5,871,984; 5,760,012; 5,888,983; 5,795,972; 5,780,296; 5,945,339; 6,004,804; and 6,010,907 and in International Publication Nos. WO 98/49350; WO 99/07865; WO 99/58723; WO 99/58702; WO 99/40789; U.S. Pat. No. 6,870,075; and US Published Patent Application 20030084473. The sequence of the SSOMV contains two regions that are homologous with the target sequence separated by a region that contains the desired genetic alteration termed the mutator region. The mutator region can have a sequence that is the same length as the sequence that separates the homologous regions in the target sequence, but having a different sequence. Such a mutator region will cause a substitution.

The nucleotides of the SSOMV are deoxyribonucleotides that are linked by unmodified phosphodiester bonds except that the 3' terminal and/or 5' terminal internucleotide linkage or alternatively the two 3' terminal and/or 5' terminal internucleotide linkages can be a phosphorothioate or phosphoamidate. As used herein an internucleotide linkage is the linkage between nucleotides of the SSOMV and does not include the linkage between the 3' end nucleotide or 5' end nucleotide and a blocking substituent, see supra. In a specific embodiment the length of the SSOMV is between 21 and 55 deoxynucleotides and the lengths of the homology regions are, accordingly, a total length of at least 20 deoxynucleotides and at least two homology regions should each have lengths of at least 8 deoxynucleotides.

The SSOMV can be designed to be complementary to either the coding or the non-coding strand of the target gene. When the desired mutation is a substitution of a single base, it is preferred that both the mutator nucleotides be a pyrimidine. To the extent that is consistent with achieving the desired functional result it is preferred that both the mutator nucleotide and the targeted nucleotide in the complementary strand be pyrimidines. Particularly preferred are SSOMV that encode transversion mutations, i.e., a C or T mutator nucleotide is mismatched, respectively, with a C or T nucleotide in the complementary strand.

In addition to the oligodeoxynucleotide the SSOMV can contain a 5' blocking substituent that is attached to the 5' terminal carbons through a linker. The chemistry of the linker is not critical other than its length, which should preferably be at least 6 atoms long and that the linker should be flexible. A variety of non-toxic substituents such as biotin, cholesterol or other steroids or a non-intercalating cationic fluorescent dye can be used. Particularly preferred as reagents to make SSOMV are the reagents sold as Cy3™ and Cy5™ by Glen Research, Sterling Va., which are blocked phosphoroamidites that upon incorporation into an oligonucleotide yield 3,3,3',3'-tetramethyl N,N'-isopropyl substituted indomonocarbocyanine and indodicarbocyanine dyes, respectively. Cy3 is the most preferred. When the indocarbocyanine is N-oxyalkyl substituted it can be conveniently linked to the 5' terminal of the oligodeoxynucleotide through as a phosphodiester with a 5' terminal phosphate. The chemistry of the dye linker between the dye and the oligodeoxynucleotide is not critical and is chosen for synthetic convenience. When the commercially available Cy3 phosphoramidite is used as directed the resulting 5' modification consists of a blocking substituent and linker together which are a N-hydroxypropyl, N'-phosphatidylpropyl 3,3,3',3'-tetramethyl indomonocarbocyanine.

In a preferred embodiment the indocarbocyanine dye is tetra substituted at the 3 and 3' positions of the indole rings. Without limitation as to theory these substitutions prevent the dye from being an intercalating dye. The identity of the substituents at these positions are not critical. The SSOMV can in addition have a 3' blocking substituent. Again the chemistry of the 3' blocking substituent is not critical.

In another preferred embodiment the recombinageneic oligonucleotide is a single-stranded oligodeoxynucleotide having a 3' end nucleotide, a 5' end nucleotide, having at least 25 deoxynucleotides and not more than 65 deoxynucleotides, and having a sequence comprising at least two regions each of at least 8 deoxynucleotides that are each, respectively, identical to at least two regions of the targeted chromosomal gene, which regions together are at least 24 nucleotides in length, and which regions are separated by at least one nucleotide in the sequence of the targeted chromosomal gene or in the sequence of the oligodeoxynucleotide or both such that the sequence of the oligodeoxynucleotide is not identical to the sequence of the targeted chromosomal gene. See U.S. Pat. No. 6,271,360 which is incorporated herein by reference.

Microcarriers and Microfibers

The use of metallic microcarriers (microspheres) for introducing large fragments of DNA into plant cells having cellulose cell walls by projectile penetration is well known to those skilled in the relevant art (henceforth biolistic delivery). U.S. Pat. Nos. 4,945,050; 5,100,792 and 5,204,253 describe general techniques for selecting microcarriers and devices for projecting them. U.S. Pat. Nos. 5,484,956 and 5,489,520 describe the preparation of fertile transgenic corn using microprojectile bombardment of corn callus tissue. The biolistic techniques are also used in transforming immature corn embryos.

Specific conditions for using microcarriers in the methods of the present invention are described in International Publication WO 99/07865. In an illustrative technique, ice cold microcarriers (60 mg/ml), mixed duplex oligonucleotide (60 mg/ml) 2.5 M $CaCl_2$ and 0.1 M spermidine are added in that order; the mixture is gently agitated, e.g., by vortexing, for 10 minutes and let stand at room temperature for 10 minutes, whereupon the microcarriers are diluted in 5 volumes of ethanol, centrifuged and resuspended in 100% ethanol. Good results can be obtained with a concentration in the adhering solution of 8-10 μg/μl microcarriers, 14-17 μg/ml mixed duplex oligonucleotide, 1.1-1.4 M $CaCl_2$ and 18-22 mM spermidine. Optimal results were observed under the conditions of 8 μg/μl microcarriers, 16.5 μg/ml mixed duplex oligonucleotide, 1.3 M $CaCl_2$ and 21 mM spermidine.

Recombinagenic oligonucleobases can also be introduced into plant cells for the practice of the present invention using microfibers to penetrate the cell wall and cell membrane. U.S. Pat. No. 5,302,523 to Coffee et al. describes the use of 30.times.0.5 μm and 10.times.0.3 μm silicon carbide fibers to facilitate transformation of suspension maize cultures of Black Mexican Sweet. Any mechanical technique that can be used to introduce DNA for transformation of a plant cell using microfibers can be used to deliver recombinagenic oligonucleobases for use in making the present EPSPS mutants. The process disclosed by Coffee et al in U.S. Pat. No. 5,302,523 can be employed with regenerable plant cell materials to introduce the present recombinagenic oligonucleobases to effect the mutation of the EPSPS gene whereby a whole mutated plant can be recovered that exhibits the glyphosate resistant phenotype.

An illustrative technique for microfiber delivery of a recombinagenic oligonucleobase is as follows: Sterile microfibers (2 μg) are suspended in 150 μl of plant culture medium containing about 10.mu.g of a mixed duplex oligonucleotide. A suspension culture is allowed to settle and equal volumes of packed cells and the sterile fiber/nucleotide suspension are vortexed for 10 minutes and plated. Selective media are applied immediately or with a delay of up to about 120 hours as is appropriate for the particular trait.

Electroporation

In an alternative embodiment, the recombinagenic oligonucleobases can be delivered to the plant cell by electroporation of a protoplast derived from a plant part according to techniques that are well-known to one of ordinary skill in the art. See, e.g., Gallois et al., 1996, in Methods in Molecular Biology 55:89-107, Humana Press, Totowa, N.J.; Kipp et al., 1999, in Methods in Molecular Biology 133:213-221, Humana Press, Totowa, N.J.

Recombinagenic oligonucleobases can also be introduced into microspores by electroporation. Upon release of the tetrad, the microspore is uninucleate and thin-walled. It begins to enlarge and develops a germpore before the exine forms. A microspore at this stage is potentially more amenable to transformation with exogenous DNA than other plant cells. In addition, microspore development can be altered in vitro to produce either haploid embryos or embryogenic callus that can be regenerated into plants (Coumans et al., Plant Cell Rep. 7:618-621, 1989; Datta et al., Plant Sci. 67:83-88, 1990; Maheshwari et al., Am. J Bot. 69:865-879, 1982; Schaeffer, Adv. In Cell Culture 7:161-182, 1989; Swanson et al., Plant Cell Rep. 6:94-97, 1987). Thus, transformed microspores can be regenerated directly into haploid plants or dihaploid fertile plants upon chromosome doubling by standard methods. See also co-pending application U.S. Ser. No. 09/680,858 entitled Compositions and Methods for Plant Genetic Modification which is incorporated herein by reference.

Microspore electroporation can be practiced with any plant species for which microspore culture is possible, including but not limited to plants in the families Graminae, Leguminoceae, Cruciferaceae, Solanaceac, Cucurbitaceae, Rosaccae, Poaceae, Lilaceae, Rutaceae, Vitaceae, including such species as corn (*Zea mays*), wheat (*Triticum aestivum*), rice (*Oryza sativa*), oats, barley, canola (*Brassica napus, Brassica rapa, Brassica oleracea*, and Brassicajuncea), cotton (*Gossypium hirsuitum* L.), various legume species (e.g., soybean [*Glycine max*], pea [*Pisum sativum*], etc.), grapes [*Vitis vinifera*], and a host of other important crop plants. Microspore embryogenesis, both from anther and microspore culture, has been described in more than 170 species, belonging to 68 genera and 28 families of dicotyledons and monocotyledons (Raghavan, Embryogenesis in Agniosperms: A Developmental and Experimental Study, Cambridge University Press, Cambridge, England, 1986; Rhagavan, Cell Differentiation 21:213-226, 1987; Raemakers et al., Euphytica 81:93-107, 1995). For a detailed discussion of microspore isolation, culture, and regeneration of double haploid plants from microspore-derived embryos [MDE] in *Brassica napus* L., see Nehlin, The Use of Rapeseed (*Brassica napus* L.) Microspores as a Tool for Biotechnological Applications, doctoral thesis, Swedish University of Agricultural Sciences, Uppsala, Sweden, 1999; also Nehlin et al., Plant Sci. 111:219-227, 1995, and Nehlin et al., Plant Sci. 111:219-227, 1995). Chromosome doubling from microspore or anther culture is a well-established technique for production of double-haploid homozogous plant lines in several crops (Heberle-Bors et al., In vitro pollen cultures: Progress and perspectives. In: Pollen Biotechnology. Gene expression and allergen characterization, vol. 85-109, ed. Mohapatra, S. S., and Knox, R. B., Chapman and Hall, New York, 1996).

Microspore electroporation methods are described in Jardinaud et al., Plant Sci. 93:177-184, 1993, and Fennell and Hauptman, Plant Cell Reports 11:567-570, 1992. Methods for electroporation of MDON into plant protoplasts can also be adapted for use in microspore electroporation.

Whiskers and Microinjection

In yet another alternative embodiment, the recombinagenic oligonucleobase can be delivered to the plant cell by whiskers or microinjection of the plant cell. The so called whiskers technique is performed essentially as described in Frame et al., 1994, Plant J. 6:941-948. The recombinagenic oligonucleobase is added to the whiskers and used to transform the plant cells. The recombinagenic oligonucleobase may be co-incubated with plasmids comprising sequences encoding proteins capable of forming recombinase complexes in plant cells such that recombination is catalyzed between the oligonucleotide and the target sequence in the EPSPS gene.

Selection of Glyphosate Resistant Plants

Plants or plant cells can be tested for resistance or tolerance to a phosphonomethylglycine herbicide using commonly known methods in the art, e.g., by growing the plant or plant cell in the presence of a phosphonomethylglycine herbicide and measuring the rate of growth as compared to the growth rate of control plants in the absence of the herbicide. In the case of glyphosate concentrations of from about 0.01 to about 20 mM are employed in selection medium.

The following examples illustrate the practice of the present invention but should not be construed as limiting its scope.

EXAMPLE 1

P178A Mutants in *Brassica napus* (Canola)

The following genoplast (recombinagenic oligonucleobase) was made to make a P178A change in *Brassica napus* (canola) germplasm:

SEQ ID 1:
VATGCAGGAACAGCCA<u>TGC</u>GTTCACTTACGGCTGCAGTTACTH wherein V is a fluorescent dye (V=Cy3) and H is a reverse nucleotide or reverse base (H=3'DMTdCCPG). The underlined nucleobases represent the heterologous region (codon) where the mutation occurs in the canola genome, ie, A. The genoplast is made according to well known techniques and the genoplast is preferably delivered into a canola plant cell via microparticle bombardment, ie, biolistics. Canola plants regenerated that contain the P178A mutant are resistant to glyphosate when applied at commercial rates.

EXAMPLE 2

P173A Mutants in *Oryza sativa* (Rice)

The following genoplast (recombinagenic oligonucleobase) was made to make a P173A change in *Oryza sativa* (rice) germplasm:

SEQ ID 2:
VGGAACGCTGGAAC<u>TGC</u>AATGCGAGCATTGACAGCAGCCGTGACTGCH wherein V is a fluorescent dye (V=Cy3) and H is a reverse nucleotide or reverse base (H=3'DMTdCCPG). The underlined nucleobases represent the heterologous region (codon) where the mutation occurs in the rice genome, ie, A. The genoplast is made according to well known techniques and the genoplast is preferably delivered into a rice plant cell via microparticle bombardment, ie, biolistics. Rice plants regenerated that contain the P173A mutant are resistant to glyphosate when applied at commercial rates.

EXAMPLE 3

*E Coli* and Arabidposis Mutants

The following table lists the EPSPS mutations in *E coli* (Area) and *Arabidopsis* NM 130093 that produce a glyphosate resistant phenotype. The specific codon change is indicated in the right column.

| | E. COLI | ARABIDOPSIS NM 130093 | MUTATION |
|---|---|---|---|
| 1. | $T_{97} \to A_{97}$ | T178A | ACA → GCA |
| 2. | $L_{82} \to S_{82}$ | F159S | TTC → TCC |
| 3. | $P_{101} \to C_{101}$ | P182C | CCA → TGC |
| 4. | $T_{97}; P_{101} \to I_{97}; A_{101}$ | T178I; P182A | (T -> I) ACA → ATA; (P -> A) CCA -> GCA |
| 5. | $*N_{194} \to A_{194}$ | N193A | AAC → GCC |
| 6. | $T_{97}; P_{101} \to A_{97}; A_{101}$ | T178A; P182A | (T -> A) ACA → GCA; (P -> A) CCA -> GCA |
| 7. | $T_{97}; P_{101} \to A_{97}; T_{101}$ | T178A; P182T | (T -> A) ACA → GCA; (P -> T) CCA -> ACA |
| 8. | $L_{82}; P_{101} \to S_{82}; A_{101}$ | F159S; P182A | (F -> S) TTC → TCC; (P -> A) CCA -> GCA |
| 9. | $L_{82}; P_{101} \to S_{82}; T_{101}$ | F159S; P182T | (F -> S) TTC → TCC; (P -> T) CCA -> ACA |

*No true homologous amino acid in *E. coli*. The closest homologous amino acid in *E. coli* is N111. Also note that the native *E coli* has an L in the 82 position and the analogous amino acid in *Arabodposis* at position 159 is F The following listing (a-g) shows in more detail the present mutations. All references to "*Arabidopsis*" are to the *Arabidopsis* gene NM 130093. The sequences are the gene sequences of the native EPSPS gene (top) and the mutated EPSPS gene (bottom). The mutated codon is bolded and underlined where the changed nucleotide is represented by a lower case letter. Sections a-g disclose SEQ ID NOS: 3-16, respectively, in order of appearance.

| a. T178A | | | |
|---|---|---|---|
| | E. COLI | ARABIDOPSIS | MUTATION |
| 1. | $T_{97} \to A_{97}$ | T178A | ACA → GCA |
| | CTTTACCTCGGTAATGCAGGAACAGCAATGCGTCCACTTACC | | |
| | CTTTACCTCGGTAATGCAGGAgCAGCAATGCGTCCACTTACC | | |

| b. F159S | | | |
|---|---|---|---|
| | E. COLI | ARABIDOPSIS | MUTATION |
| 2. | $L_{82} \to S_{82}$ | F159S | TTC → TCC |
| | GGATGTGGCGGGATATTCCCAGCTTCCATAGATTC | | |
| | GGATGTGGCGGGATATcCCCAGCTTCCATAGATTC | | |

-continued c. P101C

| | E. COLI | ARABIDOPSIS | MUTATION |
|---|---|---|---|
| 3. | P$_{101}$ → C$_{101}$ | P182C | CCA → TGC |
| | GCAGGAACAGCAATGCGTCCACTTACCGCTGCGGTC | | |
| | GCAGGAACAGCAATGCGTtgcCTTACCGCTGCGGTC | | | d. T178I; P182A

| | E. COLI | ARABIDOPSIS | MUTATION |
|---|---|---|---|
| 4. | T$_{97}$; P$_{101}$ → I$_{97}$; A$_{101}$ | T178I; P182A | (T → I) ACA → ATA; (P → A) CCA → GCA |
| | CCTCGGTAATGCAGGAACAGCAATGCGTCCACTTAC | | |
| | CCTCGGTAATGCAGGAAtAGCAATGCGTgCACTTAC | | | e. N193A

| | E. COLI | ARABIDOPSIS | MUTATION |
|---|---|---|---|
| 5. | *N$_{193}$ → A$_{193}$ | N193A | AAC → GCC |
| | GGTCACTGCTGCAGGTGGAAACGCAAGTTATGTGCTTG | | |
| | GGTCACTGCTGCAGGTGGAgcCGCAAGTTATGTGCTTG | | | f. T178A; P182A

| | E. COLI | ARABIDOPSIS | MUTATION |
|---|---|---|---|
| 6. | T$_{97}$; P$_{101}$ → A$_{97}$; A$_{101}$ | T178A; P182A | (T → A) ACA → GCA; (P → A) CCA → GCA |
| | CCTCGGTAATGCAGGAACAGCAATGCGTCCACTTAC | | |
| | CCTCGGTAATGCAGGAgCAGCAATGCGTgCACTTAC | | | g. T178A; P182T

| | E. COLI | ARABIDOPSIS | MUTATION |
|---|---|---|---|
| 7. | T$_{97}$; P$_{101}$ → A$_{97}$; T$_{101}$ | T178A; P182T | (T → A) ACA → GCA; (P → T) CCA → ACA |
| | CCTCGGTAATGCAGGAACAGCAATGCGTCCACTTAC | | |
| | CCTCGGTAATGCAGGAgCAGCAATGCGTaCACTTAC | | |

We claim:

1. An herbicide resistant plant that comprises a genomic EPSPS gene that expresses a EPSPS protein that is mutated at amino acid positions $Thr_{179}$ and $Pro_{183}$ in an Arabidopsis EPSPS protein (SEQ ID NO: 19) or at an analogous amino acid residue in an EPSPS homolog, wherein $Thr_{179}$ is changed to Ile and $Pro_{183}$ is changed to Leu or Cys.

2. A method for producing a non-transgenic, herbicide resistant or tolerant plant comprising:
   introducing into plant cells a recombinagenic oligonucleobase with a targeted mutation in the EPSPS gene to produce plant cells with a mutant genomic EPSPS gene that expresses a EPSPS protein that is mutated at amino acid positions $Thr_{179}$ and $Pro_{183}$ in an Arabidopsis EPSPS protein (SEQ ID NO: 19) or at an analogous amino acid residue in an EPSPS homolog, wherein $Thr_{179}$ is changed to Ile and $Pro_{183}$ is changed to Leu or Cys;
   selecting a plant cell exhibiting improved tolerance to glyphosate as compared to a corresponding wild-type plant cell; and
   regenerating a non-transgenic herbicide resistant or tolerant plant having a mutated EPSPS gene from said selected plant cell.

* * * * *